(12) United States Patent
Nagasawa et al.

(10) Patent No.: US 8,575,249 B2
(45) Date of Patent: Nov. 5, 2013

(54) HIGH HEAT-RESISTANT POLYGERMANE COMPOUND WITH SULFUR-CONTAINING ORGANIC GROUP

(75) Inventors: Takehiro Nagasawa, Funabashi (JP); Akira Watanabe, Sendai (JP); Tokuji Miyashita, Sendai (JP)

(73) Assignees: Nissan Chemical Industries, Ltd., Tokyo (JP); Tohoku University, Sendai-shi (JP)

( * ) Notice: Subject to any disclaimer, the term of this patent is extended or adjusted under 35 U.S.C. 154(b) by 0 days.

(21) Appl. No.: 13/579,188

(22) PCT Filed: Feb. 16, 2011

(86) PCT No.: PCT/JP2011/053264
§ 371 (c)(1),
(2), (4) Date: Oct. 4, 2012

(87) PCT Pub. No.: WO2011/102375
PCT Pub. Date: Aug. 25, 2011

(65) Prior Publication Data
US 2013/0059951 A1 Mar. 7, 2013

(30) Foreign Application Priority Data
Feb. 16, 2010 (JP) .................. 2010-031877

(51) Int. Cl.
*C07F 7/30* (2006.01)
*C08K 5/56* (2006.01)
(52) U.S. Cl.
USPC .............................. 524/175; 556/81; 528/381
(58) Field of Classification Search
USPC .............................. 524/175; 556/81; 528/381
See application file for complete search history.

(56) References Cited

FOREIGN PATENT DOCUMENTS

| JP | A 61-291650 | 12/1986 |
| JP | A 4-363328 | 12/1992 |
| JP | A 2008-44835 | 2/2008 |
| JP | A 2009-145872 | 7/2009 |

OTHER PUBLICATIONS

Kobayashi et al. Macromol. Symp. 98, 91-100 (1995). Novel Polymerizations of Germylenes and Their Reaction Mechanisms.*
Riviere et al; "Polygermanes Precurseurs D'especes Du Germanium A Coordinance Non Usuelle;" *Journal of Organometallic Chemistry*; (1984) vol. 264 No. 1-2; pp. 193-206; (with English-language abstract).
Translation of May 17, 2011 Written Opinion issued in International Application No. PCT/JP2011/053264.
May 17, 2011 Search Report issued in International Patent Application No. PCT/JP2011/053264.

\* cited by examiner

*Primary Examiner* — John Uselding
(74) *Attorney, Agent, or Firm* — Oliff & Berridge, PLC (57) ABSTRACT

There is provided a polygermane compound forming a film having a high refractive index and thermal stability, and containing a sulfur atom-containing organic group as a group bonded to a germanium atom. A polygermane compound comprising a sulfur atom-containing organic group as a group bonded to a germanium atom, in which the sulfur atom-containing organic group is a group of Formula [1]:

-L-Z    [1]

where L is a single bond, a $C_{1-6}$ alkylene group, or a $C_{4-20}$ arylene group optionally substituted with a $C_{1-6}$ alkyl group; and Z is a $C_{1-20}$ sulfide group, a $C_{1-14}$ cyclic sulfide group optionally substituted with a $C_{1-6}$ alkyl group, a $C_{2-20}$ alkyl group containing a sulfide bond, or a $C_{5-20}$ aralkyl group containing a sulfide bond, with a proviso that when L is a single bond, Z is not a $C_{1-20}$ sulfide group.

12 Claims, 2 Drawing Sheets

HIGH HEAT-RESISTANT POLYGERMANE COMPOUND WITH SULFUR-CONTAINING ORGANIC GROUP

TECHNICAL FIELD

The present invention relates to a polygermane compound and a thin film containing the same, a resin composition containing the polygermane compound, and a resin molded article containing the same. More in detail, the present invention relates to a polygermane compound having a high refractive index and thermal stability and containing a sulfur atom-containing organic group as a group bonded to a germanium atom and a thin film containing the same, a resin composition containing the polygermane compound, and a resin molded article produced from the same.

BACKGROUND ART

In various parts of photoelectronic devices and recording materials, organic polymer materials and organic polymer thin films are used. They are usually produced by using a carbon-based polymer compound having a refractive index of 1.7 or less. In recent years, according to densification of photoelectronic devices or capacity enlargement of recording materials, it is considered that an optical process having a higher numerical aperture (NA) is necessary to be applied. Therefore, also for such organic polymer materials, it is required to have a high refractive index.

As an attempt to make an organic polymer material having a high refractive index, the development of a polymer material containing a polymer compound having, besides a carbon atom, a bromine atom or a sulfur atom is performed. However, by such a technique, a polymer material having a refractive index of over 1.8 has not been yet obtained.

For the purpose of making a polymer material having a further higher refractive index, there is disclosed a resin formed from a high refractive index resin composition in which fine particles of a metal oxide are dispersed in a polymer. For example, there is reported that in a resin formed from a resin composition in which 50% by weight of zirconia ($ZrO_2$) fine particles (having a refractive index of 2.1 in a bulk state) are dispersed in an allyl ether isophthalate resin (having a refractive index of 1.56), it has been calculated that a refractive index of 1.83 can be obtained (see Patent Document 1).

Thus, it is known that a resin in which a metal oxide well known as a substance having a high refractive index is dispersed has a high refractive index. In such a resin, light scattering occurs due to aggregation of metal oxides with each other, so that the resin is likely to be unsuitable for the optical material. For obtaining a homogeneous inorganic fine particles-dispersed resin causing no light scattering capable of solving the above disadvantage, a precise control over the particle diameter of the inorganic fine particle and the organic substituent for surface modification is necessary. In addition, addition of a large quantity of inorganic fine particles to the resin composition for obtaining a resin with high refractive index causes not only a problem of the increased viscosity, but also a fear of impaired transparency (see Patent Document 2).

As a method for solving such a problem of dispersibility of the inorganic fine particle and obtaining a polymer material with high refractive index, there is proposed a method of using a polymer compound in which a metalloid element or metal element with a large atomic number contributing to obtaining a high refractive index is incorporated through a chemical bond.

As an example of such a polymer compound, a polygermane compound having the backbone containing a Ge—Ge bond is reported (Patent Document 3). The polygermane compound is dissolved in a solvent or a resin, so that the polygermane compound can form a homogeneous film causing no light scattering and the film formed therefrom has a high refractive index of approximately 1.8.

RELATED-ART DOCUMENT

Patent Document

Patent Document 1: Japanese Patent Application Publication No. 61-291650 (JP 61-291650 A)
Patent Document 2: Japanese Patent Application Publication No. 2008-44835 (JP 2008-44835 A)
Patent Document 3: Japanese Patent Application Publication No. 2009-145872 (JP 2009-145872 A)

SUMMARY OF THE INVENTION

Problem to be Solved by the Invention

However, the film described in Patent Document 3 has low thermal stability, so that the film has a problem in that after a heating treatment or during the use under a high temperature condition, the refractive index thereof is lowered.

The present invention has been completed in view of such situations and it is an object of the present invention to provide a polygermane compound forming a film having an extremely high refractive index and thermal stability by which the refractive index of the film is not lowered even at a high temperature, and containing a sulfur atom-containing organic group as a group bonded to a germanium atom.

It is another object of the present invention to provide: a polygermane compound which is not aggregated when the compound is mixed with a resin, which has excellent dispersibility, and which contains a sulfur atom-containing organic group as a group bonded to a germanium atom; a resin composition containing the polygermane compound; and a highly transparent resin produced from the resin composition in which the refractive index is enhanced.

Means for Solving the Problem

As a result of assiduous research intended to overcome these disadvantages, the inventors of the present invention have found that a thin film containing a polygermane compound containing a sulfur atom-containing organic group as a group bonded to a germanium atom has a high refractive index and heat resistance by which the refractive index thereof is not lowered even after a heating treatment or during the use under a high temperature condition to complete the present invention.

That is, the present invention, as a first aspect, relates to a polygermane compound containing a sulfur atom-containing organic group as a group bonded to a germanium atom.

As a second aspect, the present invention relates to the polygermane compound according to the first aspect in which the sulfur atom-containing organic group is a group of Formula [1]:

$$-L-Z \quad [1]$$

(where L is a single bond, a $C_{1-6}$ alkylene group, or a $C_{4-20}$ arylene group optionally substituted with a $C_{1-6}$ alkyl group; and Z is a $C_{1-20}$ sulfide group, a $C_{1-14}$ cyclic sulfide group optionally substituted with a $C_{1-6}$ alkyl group, a $C_{2-20}$ alkyl group containing a sulfide bond, or a $C_{5-20}$ aralkyl group containing a sulfide bond, with a proviso that when L is a single bond, Z is not a $C_{1-20}$ sulfide group).

As a third aspect, the present invention relates to the polygermane compound according to the second aspect in which Z is a $C_{1-20}$ sulfide group.

As a fourth aspect, the present invention relates to the polygermane compound according to the second aspect in which Z is a $C_{1-4}$ 5-membered ring cyclic sulfide group optionally substituted with a $C_{1-6}$ alkyl group.

As a fifth aspect, the present invention relates to the polygermane compound according to the second aspect in which L is a thienylene group optionally substituted with a $C_{1-6}$ alkyl group.

As a sixth aspect, the present invention relates to a polygermane compound that contains a sulfur atom-containing organic group of Formula [1] as a group bonded to a germanium atom. The polygermane compound is obtained by reacting an alkali metal or an alkaline earth metal with a germanium tetrahalide and by further reacting the resultant product with a sulfur atom-containing halide of Formula [2].

(where L is a single bond, a $C_{1-6}$ alkylene group, or a $C_{4-20}$ arylene group optionally substituted with a $C_{1-6}$ alkyl group; Z is a $C_{1-20}$ sulfide group, a $C_{1-14}$ cyclic sulfide group optionally substituted with a $C_{1-6}$ alkyl group, a $C_{2-20}$ alkyl group containing a sulfide bond, or a $C_{5-20}$ aralkyl group containing a sulfide bond; and X is a halogen atom, with a proviso that when L is a single bond, Z is not a $C_{1-20}$ sulfide group).

As a seventh aspect, the present invention relates to the polygermane compound according to the sixth aspect in which Z is a $C_{1-20}$ sulfide group.

As an eighth aspect, the present invention relates to the polygermane compound according to the sixth aspect in which Z is a $C_{1-4}$ 5-membered ring cyclic sulfide group optionally substituted with a $C_{1-6}$ alkyl group.

As a ninth aspect, the present invention relates to the polygermane compound according to the sixth aspect in which L is a thienylene group optionally substituted with a $C_{1-6}$ alkyl group.

As a tenth aspect, the present invention relates to a varnish containing the polygermane compound as described in any one of the first aspect to the ninth aspect.

As an eleventh aspect, the present invention relates to a thin film composed of the polygermane compound as described in any one of the first aspect to the ninth aspect.

As a twelfth aspect, the present invention relates to a resin composition containing the polygermane compound as described in any one of the first aspect to the ninth aspect and a thermoplastic resin and/or a curable resin.

As a thirteenth aspect, the present invention relates to a resin molded article produced from the resin composition as described in the twelfth aspect.

Effects of the Invention

The thin film containing the polygermane compound of the present invention, containing a sulfur atom-containing organic group as a group bonded to a germanium atom has transparency and further, has a refractive index higher than that of a thin film containing a conventional polygermane compound and thermal stability by which lowering of the refractive index is small even after a heating treatment or during the use under a high temperature condition, compared with a thin film containing a conventional polygermane compound.

In addition, the polygermane compound of the present invention, containing a sulfur atom-containing organic group as a group bonded to a germanium atom has excellent dispersibility relative to a resin, so that the polygermane compound causes no aggregation when being mixed with a resin and a resin obtained from a resin composition containing the polygermane compound has high transparency, a high refractive index, and high thermal stability.

Therefore, a thin film containing the polygermane compound of the present invention and a resin containing the polygermane compound of the present invention can be utilized in an optical material such as a microlens, a core material of a light waveguide, a material for a high-density photoelectronic device, and a large capacity recording material.

MODES FOR CARRYING OUT THE INVENTION

Hereinafter, the present invention is described further in detail.
<Polygermane Compound>

The polygermane compound of the present invention refers to a polymer having a Ge—Ge bond as the backbone thereof. The polygermane compound of the present invention may have any one of a linear structure and a branched structure and has preferably a branched structure. In addition, the polygermane compound contains a germanium atom bonded to a group of Formula [1] below:

In Formula [1], L is a single bond, a $C_{1-6}$ alkylene group, or a $C_{4-20}$ arylene group optionally substituted with a $C_{1-6}$ alkyl group.

In Formula [1], Z is a $C_{1-20}$ sulfide group, a $C_{1-14}$ cyclic sulfide group optionally substituted with a $C_{1-6}$ alkyl group, a $C_{2-20}$ alkyl group containing a sulfide bond, or a $C_{5-20}$ aralkyl group containing a sulfide bond.

It should be noted that when L is a single bond, Z is not a $C_{1-20}$ sulfide group in Formula [1].

The $C_{1-6}$ alkylene group as L may be a group having any structure of a linear structure, a branched structure, and a cyclic structure and examples thereof include a methylene group, an ethylene group, an n-propylene group, a tetramethylene group, a pentamethylene group, a hexamethylene group, a dimethylmethylene group, a methylethylene group, a dimethylethylene group, a dimethylpropylene group, a cyclopropylene group, and a cyclohexylene group.

The $C_{4-20}$ arylene group as L is a divalent substituent of an aromatic compound and examples thereof include a divalent substituent such as benzene, biphenyl, o-terphenyl, m-terphenyl, p-terphenyl, fluorene, naphthalene, 1-phenylnaphthalene, 2-phenylnaphthalene, anthracene, pyrene, furan, benzofuran, thiophene, benzothiophene, and dibenzothiophene.

Examples of the $C_{1-6}$ alkyl group optionally substituting a $C_{4-20}$ arylene group as L include a methyl group, an ethyl group, an n-propyl group, an isopropyl group, a cyclopropyl group, an n-butyl group, an isobutyl group, a sec-butyl group, a tert-butyl group, a cyclobutyl group, an n-pentyl group, a 2-methylbutyl group, an isopentyl group, a neopentyl group, a sec-isoamyl group, a tert-pentyl group, a cyclopentyl group, an n-hexyl group, a 1-methylpentyl group, an isohexyl group, a neohexyl group, a 2,3-dimethylbutyl group, a 1,1,2-trimethylpropyl group, and a cyclohexyl group.

L is preferably a single bond, a phenylene group, or a thienylene group.

Examples of the $C_{1-20}$ sulfide group as Z include a methylthio group, an ethylthio group, an n-propylthio group, an isopropylthio group, a cyclopropylthio group, an n-butylthio group, an isobutylthio group, a sec-butylthio group, a tert-butylthio group, a cyclobutylthio group, an n-pentylthio group, a 2-methylbutylthio group, an isopentylthio group, a neopentylthio group, a sec-isoamylthio group, a tert-pentylthio group, a cyclopentylthio group, an n-hexylthio group, a 1-methylpentylthio group, an isohexylthio group, a neohexylthio group, a 2,3-dimethylbutylthio group, a 1,1,2-trimethylpropylthio group, a cyclohexylthio group, a heptylthio group, an octylthio group, a nonylthio group, a decylthio group, an undecylthio group, a dodecylthio group, an icosylthio group, an adamantylthio group, a benzylthio group, a phenethylthio group, a 1-naphthylmethylthio group, a 2-naphthylmethylthio group, a 2-thienylmethylthio group, a 3-thienylmethylthio group, a phenylthio group, a 1-naphthylthio group, a 2-naphthylthio group, a 2-thienylthio group, and a 3-thienylthio group.

Examples of the $C_{1-14}$ cyclic sulfide group as Z include a substituent having a monocyclic, a condensed cyclic, a polycyclic, or a crosslinked cyclic structure and containing a sulfur atom as an atom constituting a ring. Examples of the substituent having a cyclic structure include a thiiranyl group, a dithiiranyl group, a thietanyl group, a 1,2-dithietanyl group, a 1,3-dithietanyl group, a trithietanyl group, a 2-thiolanyl group, a 3-thiolanyl group, a 1,2-dithiolanyl group, a 1,3-dithiolanyl group, a 1,2,3-trithiolanyl group, a 1,2,4-trithiolanyl group, a tetrathiolanyl group, a thianyl group, a 1,2-dithianyl group, a 1,3-dithianyl group, a 1,4-dithianyl group, a 1,2,3,-trithianyl group, a 1,2,4-trithianyl group, a 1,3,5-trithianyl group, a 1,2,3,4-tetrathianyl group, a 1,2,4,5-tetrathianyl group, a pentathianyl group, a thiepanyl group, a 1,2-dithiepanyl group, a 1,3-dithiepanyl group, a 1,4-dithiepanyl group, a 1,2,3-trithiepanyl group, a 1,2,4-trithiepanyl group, a 1,2,5-trithiepanyl group, a 1,3,5-trithiepanyl group, a 1,2,3,4-tetrathiepanyl group, a 1,2,3,5-tetrathiepanyl group, a 1,2,4,5-tetrathiepanyl group, a 1,2,4,6-tetrathiepanyl group, a 1,2,3,4,5-pentathiepanyl group, a 1,2,3,4,6-pentathiepanyl group, a 1,2,3,5,6-pentathiepanyl group, a hexathiepanyl group, a 2-thienyl group, a 3-thienyl group, a 2-benzothienyl group, a 3-benzothienyl group, and a dibenzothienyl group.

Examples of the $C_{1-6}$ alkyl group optionally substituting a $C_{1-14}$ cyclic sulfide group as Z include the same examples as the examples of the above $C_{1-6}$ alkyl group optionally substituting the $C_{4-20}$ arylene group.

Examples of the $C_{2-20}$ alkyl group containing a sulfide bond as Z include a methylthiomethyl group, an ethylthiomethyl group, an n-propylthiomethyl group, an isopropylthiomethyl group, a cyclopropylthiomethyl group, an n-butylthiomethyl group, an isobutylthiomethyl group, a sec-butylthiomethyl group, a tert-butylthiomethyl group, a cyclobutylthiomethyl group, an n-pentylthiomethyl group, a 2-methylbutylthiomethyl group, an isopentylthiomethyl group, a neopentylthiomethyl group, a sec-isoamylthiomethyl group, a tert-pentylthiomethyl group, a cyclopentylthiomethyl group, an n-hexylthiomethyl group, a 1-methylpentylthiomethyl group, an isohexylthiomethyl group, a neohexylthiomethyl group, a 2,3-dimethylbutylthiomethyl group, a 1,1,2-trimethylpropylthiomethyl group, a cyclohexylthiomethyl group, an adamantylthiomethyl group, a (methylthiomethylthio)methyl group, an (ethylthiomethylthio)methyl group, a ((methylthiomethylthio)methylthio)methyl group, an ((ethylthiomethylthio)methylthio)methyl group, a 2-(ethylthio)ethyl group, a 2-(2-(methylthio)ethylthio)ethyl group, a 2-(2-(ethylthio)ethylthio)ethyl group, a 2-(2-(propylthio)ethylthio)ethyl group, and a 2-(2-(2-(ethylthio)ethylthio)ethylthio)ethyl group.

Examples of the $C_{5-20}$ aralkyl group containing a sulfide bond as Z include a phenylthiomethyl group, 1-naphthylthiomethyl group, a 2-naphthylthiomethyl group, a 2-thienylthiomethyl group, a 3-thienylthiomethyl group, a benzylthiomethyl group, a phenethylthiomethyl group, a 1-naphthylmethylthiomethyl group, a 2-naphthylmethylthiomethyl group, a 2-thienylmethylthiomethyl group, and a 3-thienylmethylthiomethyl group.

Z is preferably a sulfide group or a cyclic sulfide group, particularly preferably a $C_{1-6}$ alkylthio group and a 5-membered ring cyclic sulfide group, and most preferably a methylthio group, a 2-thienyl group, and a 5-methyl-2-thienyl group.

Preferred examples of the combination of L and Z include a combination in which L is a single bond and Z is a $C_{1-14}$ cyclic sulfide group, preferably an aromatic cyclic sulfide group, and a combination in which L is a $C_{4-20}$ arylene group optionally substituted with a $C_{1-6}$ alkyl group, preferably a phenylene group or a thienylene group and Z is a $C_{1-20}$ sulfide group.

The -L-Z group is preferably a sulfur atom-containing organic group in which an atom bonded to a germanium atom in the -L-Z group is an atom constituting a ring structure, more preferably an aromatic ring structure.

<Production Method of Polygermane Compound>

The production method of the polygermane compound of the present invention, containing a sulfur atom-containing organic group as a group bonded to a germanium atom is not particularly limited and examples thereof include a method including: reacting a germanium halide in the presence of an alkali metal or an alkaline earth metal; and reacting the resultant product with a sulfur atom-containing halide.

As the germanium halide used as a raw material in the above reaction, a germanium tetrahalide, a germanium trihalide, and a germanium dihalide can be used. The germanium halides may be used individually or in combination of two or more types thereof. From the viewpoint of the number of bonding, a germanium tetrahalide such as germanium tetrafluoride, germanium tetrachloride, germanium tetrabromide, and germanium tetraiodide is preferred and from the viewpoints of the reaction control and the cost, germanium tetrachloride is particularly preferred.

By reacting the germanium halide in the presence of an alkali metal or an alkaline earth metal, a polygermane having a Ge—Ge bond can be obtained.

Examples of the alkali metal used here include lithium, sodium, and potassium and examples of the alkaline earth metal used here include beryllium, magnesium, and calcium. From the viewpoint of handling property, magnesium is preferred to be used.

Although the used amount of the alkali metal or the alkaline earth metal is not particularly limited, they are preferably used in an amount of 2 to 8 mole equivalents relative to the germanium halide.

Next, a terminal of the obtained polygermane is converted from a halogen into a sulfur atom-containing organic group. This conversion reaction is effected, for example, by reacting a polygermane compound having a halogen terminal with a sulfur atom-containing halide in the presence of an alkali metal or an alkaline earth metal.

Examples of the sulfur atom-containing halide used for the reaction include a compound of Formula [2] below:

$$X\text{-}L\text{-}Z \qquad [2].$$

In Formula [2], X is a halogen atom and L and Z are the same as defined above.

Examples of the halogen atom in Formula [2] include a chlorine atom, a bromine atom, and an iodine atom. Particularly, from the viewpoint of the reaction control, a bromine atom is preferred.

Although the amount of the sulfur atom-containing halide of Formula [2] used for the reaction is not particularly limited, the amount is preferably 0.5 to 4 mole equivalents relative to a germanium tetrahalide.

As the solvent used for the reaction, various solvents can be used so long as the solvent does not affect the reaction.

Examples of the usable solvent include: an aliphatic hydrocarbon solvent such as n-pentane, n-hexane, n-heptane, n-octane, and cyclohexane; an ether solvent such as diethyl ether, diisopropyl ether, dibutyl ether, cyclopentyl methyl ether, tetrahydrofuran, and 1,4-dioxane; and an aromatic hydrocarbon solvent such as benzene, toluene, xylene, and mesitylene.

These solvents may be used individually or if necessary, as a solvent mixture of two or more types thereof.

The amount of the solvent used for the reaction is not particularly limited so long as the reactants can be dissolved in the solvent, and the amount is preferably an amount of 3 to 30 times the mass of the germanium tetrahalide. When the amount is less than 3 times the mass of the germanium tetrahalide, the reaction system is solidified by by-produced inorganic salts, so that the reaction is difficultly progressed. When the amount is more than 30 times the mass of the germanium tetrahalide, by an excessive dilution, the reactivity may remarkably be lowered.

The temperature during the reaction is preferably 10° C. or more and a boiling point of the solvent or less. When the temperature is lower than 10° C., the reaction rate is remarkably lowered.

Although the reaction time is varied depending on the used raw material, particularly the sulfur atom-containing halide, it is preferably generally 3 to 24 hours.

If necessary, an activating agent for activating the reaction may be added. Examples of the activating agent include a halogen molecule such as bromine and iodine and a halogenated alkyl such as dibromoethane and diiodoethane. Although the amount of the activating agent is not particularly limited, it is preferably 0.5 mole equivalents or less, relative to the alkali metal or the alkaline earth metal.

Although the purifying method of the product obtained after the completion of the reaction is not particularly limited, purification by reprecipitation is preferred.

<Varnish Containing Polygermane Compound>

The polygermane compound of the present invention may be dissolved in a solvent to be used as a varnish.

The solvent used for the varnish may be a solvent capable of dispersing the polygermane compound without causing aggregation thereof, and examples thereof include: an ester solvent such as diethyl oxalate, ethyl acetoacetate, ethyl acetate, isobutyl acetate, ethyl butyrate, ethyl lactate, ethyl 3-methoxypropionate, methyl 2-hydroxyisobutyrate, and 4-butyrolactone; a ketone solvent such as ethyl methyl ketone, isobutyl methyl ketone, 2-hexanone, and cyclohexanone; a propylene glycol solvent such as propylene glycol monomethyl ether and propylene glycol monomethyl ether acetate; a cellosolve solvent such as methylcellosolve and methylcellosolve acetate; an ether solvent such as dibutyl ether, tetrahydrofuran, and 1,4-dioxane; an alcohol solvent such as ethanol, isopropanol, and isopentyl alcohol; an aromatic hydrocarbon solvent such as toluene and xylene; and a halogenated hydrocarbon solvent such as dichloromethane, chloroform, 1,2-dichloroethane, and trichloroethylene.

These solvents may be used individually or if necessary, as a solvent mixture of two or more types thereof.

The reaction mixture after the completion of the reaction as it is (without isolating the polygermane compound) may be prepared as the varnish. At this time, to the varnish, the above solvent can further be added.

In the varnish obtained in the present invention, the concentration of the polygermane compound in the varnish is preferably 1 to 50% by mass, further preferably 5 to 30% by mass, based on the total mass of the varnish.

<Thin Film Containing Polygermane Compound>

The thin film containing the polygermane compound of the present invention can be obtained by applying the varnish containing the polygermane compound to a base material and then, if necessary, by drying the resultant coating.

Examples of the base material to which the varnish is applied include: a plastic such as a polycarbonate, a polymethacrylate, a polystyrene, a polyester, a polyolefin, an epoxy, an acryl, a melamine, a triacetylcellulose, an ABS, an AS, and a norbornene-based resin; a metal; a glass; a ceramic; and a silicon.

The applying method of the varnish to the base material may be a known method and examples thereof include a roll coating method, a micro-gravure coating method, a gravure coating method, a flow coating method, a bar coating method, a spray coating method, a die coating method, a spin coating method, a dip coating method, a doctor blade method, and a Langmuir-Blodgett method.

Among these applying methods, by considering the balance between the productivity, the property of controlling the film thickness, and the yield, the optimal applying method can be determined.

Although the drying temperature is not limited, it is preferably 40 to 150° C. Among these temperatures, by considering the solvent species, the solvent amount, the productivity, and the like, the optimal drying temperature can be determined.

The thin film containing the polygermane compound of the present invention has a high refractive index and has thermal stability by which lowering of the refractive index is small even after a heating treatment or during the use under a high temperature condition.

<Resin Composition>

The present invention also relates to a composition of the polygermane compound with a thermoplastic resin and/or a curable resin.

In the present invention, the thermoplastic resin refers to a resin which becomes softened by being heated to the glass transition temperature thereof or the melting point thereof and which can be molded into an intended shape, or a mixture of the resin. The thermoplastic resin may contain any additive as appropriate.

In the present invention, the curable resin refers to a thermocurable resin polymerized by being heated to form a polymer network structure, a photocurable resin polymerized by being irradiated with light to form a polymer network structure, and a mixture of these resins. The curable resin may contain an additive such as a crosslinker and an initiator.

Although specific examples of the resin mixed with the polygermane compound to be used are not particularly limited, specific examples of the thermoplastic resin include: a polyolefin-based resin such as PE (polyethylene), PP (polypropylene), EVA (ethylene-vinyl acetate copolymer), and EEA (ethylene-ethyl acrylate copolymer); a polystyrene-based resin such as PS (polystyrene), HIPS (high-impact polystyrene), AS (acrylonitrile-styrene copolymer), ABS (acrylonitrile-butadiene-styrene copolymer), and MS (methyl methacrylate-styrene copolymer); a polycarbonate resin; a vinyl chloride resin; a polyamide resin; a polyimide resin; a (meth)acrylic resin such as PMMA (poly(methyl methacrylate)); a polyester resin such as PET (poly(ethylene terephthalate)), poly(butylene terephthalate), poly(ethylene naphthalate), poly(butylene naphthalate), PLA (poly(lactic acid)), poly(3-hydroxybutyric acid), polycaprolactone, poly(butylene succinate), and poly(ethylene succinate/adipate); a poly(phenylene ether) resin; a modified poly(phenylene ether) resin; a polyacetal resin; a polysulfone resin; a poly(phenylene sulfide) resin; a poly(vinyl alcohol) resin; a poly(glycolic acid); a denatured starch; cellulose acetate; cellulose triacetate; chitin; chitosan; and lignin.

Examples of the curable resin include: a thermocurable resin such as a phenol resin, a urea resin, a melamine resin, an unsaturated polyester resin, a polyurethane resin, an epoxy resin, and a silicon resin; and a photocurable resin such as an acrylic resin, an epoxyacrylic resin, and a silicon resin.

By mixing the above resin with the polygermane compound of the present invention, the resin composition is obtained. By applying the obtained resin to a base material or the like and by curing the resultant resin, the cured film containing the polygermane compound is formed.

Although the amount of the resin in the resin composition of the present invention is not particularly limited, it is preferably in a range of 1 to 10,000 parts by mass, more preferably in a range of 1 to 1,000 parts by mass, relative to 100 parts by mass of the polygermane compound, to be used.

By adjusting the mixing ratio of the polygermane compound and the resin in the resin composition, the refractive index, thermal stability, and transparency of the formed resin can be adjusted as appropriate.

Although the resin to be mixed with the polygermane compound of the present invention is not limited, examples thereof include a resin for which transparency, a high refractive index, and heat resistance are required as an optical material such as a (meth)acrylic resin.

In the case of the composition with the (meth)acrylic resin, the composition can be obtained by mixing a (meth)acrylate compound with the polygermane compound and by polymerizing the (meth)acrylate compound.

Examples of the (meth)acrylate compound used for the (meth)acrylic resin include methyl(meth)acrylate, ethyl (meth)acrylate, ethylene glycol di(meth)acrylate, tetraethylene glycol di(meth)acrylate, polyethylene glycol di(meth) acrylate, propylene glycol di(meth)acrylate, poly(propylene glycol) di(meth)acrylate, 1,4-butanediol di(meth)acrylate, 1,6-hexanediol di(meth)acrylate, neopentyl glycol di(meth) acrylate, trimethylolpropane trioxyethyl(meth)acrylate, tricyclodecanedimethanol di(meth)acrylate, tricyclodecanyl di(meth)acrylate, trimethylolpropane trioxypropyl(meth) acrylate, tris-2-hydroxyethylisocyanurate tri(meth)acrylate, tris-2-hydroxyethylisocyanurate di(meth)acrylate, 1,9-nonanediol di(meth)acrylate, pentaerythritol di(meth)acrylate, glycerin methacrylate acrylate, pentaerythritol tri(meth) acrylate, trimethylolpropane trimethacrylate, allyl(meth) acrylate, vinyl(meth)acrylate, epoxy (meth)acrylate, polyester (meth)acrylate, and urethane(meth)acrylate.

The polymerization of the (meth)acrylate compound can be performed by irradiating with light or heating, if necessary in the presence of a photo-radical initiator or a thermo-radical initiator.

Examples of the photo-radical polymerization initiator include acetophenones, benzophenones, Michler's ketones, amyloxime esters, tetramethylthiuram monosulfides, and thioxanthones.

Particularly, a photo cleavage-type photo-radical polymerization initiator is preferred. With respect to the photo cleavage-type photo-radical polymerization initiator, there is described in "Up-to-Date UV Curing Technology" (*Saishin UV Koka Gijutsu*) (p. 159; published by Technical Information Institute Co., Ltd., Kazuhiro Takausu in 1991).

Examples of the commercially available photo-radical polymerization initiator include: products manufactured by BASF Corporation, trade names: IRGACURE 184, 369, 651, 500, 819, 907, 784, 2959, CGI1700, CGI1750, CGI1850, CG24-61, DAROCUR 1116, 1173, and LUCIRIN TPO; products manufactured by UCB S.A., trade name: Ubecryl P36; and products manufactured by Fratelli Lamberti, S.p.A., trade names: ESACURE KIP150, KIP65LT, KIP100F, KT37, KT55, KT046, and KIP75/B.

The used amount of the photopolymerization initiator is preferably in a range of 15 parts by mass or less, more preferably in a range of 10 parts by mass or less, relative to 100 parts by mass of the (meth)acrylate compound, to be used.

Although the thermo-radical polymerization initiator is not particularly limited, examples thereof include: peroxides such as acetyl peroxide, benzoyl peroxide, methyl ethyl ketone peroxide, cyclohexanone peroxide, hydrogen peroxide, tert-butyl hydroperoxide, cumene hydroperoxide, di-tert-butyl peroxide, dicumyl peroxide, dilauroyl peroxide, tert-butyl peroxy acetate, tert-butyl peroxy pivalate, and tert-butyl peroxy-2-ethylhexanoate; azo-based compounds such as 2,2'-azobisisobutyronitrile, 2,2'-azobis(2,4-dimethylvaleronitrile), (1-phenylethyl)azodiphenylmethane, 2,2'-azobis (4-methoxy-2,4-dimethylvaleronitrile), dimethyl 2,2'-azobisisobutyrate, 2,2'-azobis(2-methylbutyronitrile), 1,1'-azobis (1-cyclohexanecarbonitrile), 2-(carbamoylazo) isobutyronitrile, 2,2'-azobis(2,4,4-trimethylpentane), 2-phenylazo-2,4-dimethyl-4-methoxyvaleronitrile, and 2,2'-azobis(2-methylpropane); and persulfates such as ammonium persulfate, sodium persulfate, and potassium persulfate.

The used amount of the thermopolymerization initiator is preferably in a range of 15 parts by mass or less, more preferably in a range of 10 parts by mass or less, relative to 100 parts by mass of the (meth)acrylate compound, to be used.

<Resin Molded Article>

The resin molded article of the present invention can be obtained by molding the above resin composition containing the polygermane compound according to a conventional general resin molding method.

Specifically, in the case of a resin composition containing a thermoplastic resin as the resin, the resin molded article can be obtained by heating the resin composition to melt or soften the resin composition, or in the case of a resin composition containing a curable resin, the resin molded article can be obtained by heating or irradiating with light the above resultant resin molded article to thermo-cure or photo-cure the above resin molded article.

Particularly, by containing the polygermane compound, the resin composition of the present invention has high thermal stability, so that even when the resin composition is subjected to the above heating treatment or curing treatment, a resin molded article in which a high refractive index and high transparency are maintained can be obtained.

Furthermore, by containing the polygermane compound, even when the resin molded article of the present invention is used under a high temperature condition, a high refractive index and high transparency thereof can be maintained.

EXAMPLES

Hereinafter, the present invention is more specifically described referring to Examples and Comparative Examples which should not be construed as limiting the scope of the present invention. Measuring apparatuses used in Examples are as follows.
[$^1$H NMR]
Model: JNM-ECX 300; manufactured by JEOL Ltd.
Measuring solvent: $CDCl_3$
Standard substance: tetramethylsilane (0.00 ppm)
[GPC]
Apparatus: HLC-8200 GPC; manufactured by Tosoh Corporation
Column: Shodex (registered trademark) KF-804L+KF-805L
Reference column: Shodex (registered trademark) GPC KF-800 RH×2 columns
Column temperature: 40° C.
Detector: RI
Eluent: tetrahydrofuran
Column flow rate: 1.0 mL/min
Reference column flow rate: 1.0 mL/min
[Spin Coater]
Model: 1H-D7; manufactured by Mikasa Co., Ltd.
[Ellipsometer]
Model: high-speed spectroscopic ellipsometer M2000-VI; manufactured by J.A. Woollam Japan Co., Inc.
[Prism Coupler]
Model: 2010; manufactured by Metricon Corporation Example 1

Synthesis of 2-thienyl Group-Substituted Polygermane Compound

In a nitrogen atmosphere, into a 100 mL four-neck flask, 1.8 g (75 mmol) of magnesium powder [manufactured by Kanto Chemical Co., Inc.] and 40 g of tetrahydrofuran (hereinafter, abbreviated as THF) were charged and into the resultant mixture, 3.5 g (19 mmol) of dibromoethane [manufactured by Tokyo Chemical Industry Co., Ltd.] was dropped, followed by stirring the resultant mixture at room temperature (about 25° C.) for 10 minutes. Next, into the reaction mixture, a mixture of 4.0 g (19 mmol) of germanium tetrachloride [manufactured by Yamanaka Hutech Co., Ltd.] and 12 g of THF was dropped and the resultant mixture was stirred at room temperature (about 25° C.) for 30 minutes. Into the reaction mixture, a mixture of 4.7 g (28 mmol) of 2-bromothiophene [manufactured by Tokyo Chemical Industry Co., Ltd.] and 2 g of THF was further dropped. The resultant mixture was stirred at room temperature (about 25° C.) for 18 hours and the reaction solution was charged into 200 g of methanol to reprecipitate, followed by filtering the deposited solid. The obtained solid was dissolved in 80 g of toluene and an insoluble matter was filtered off. The solvent of the filtrate was distilled off and the resultant residue was redissolved in 4 g of chloroform, followed by charging the resultant solution into 100 g of methanol to reprecipitate again. The deposited solid was filtered to obtain 1.0 g of a 2-thienyl group-substituted polygermane compound (hereinafter, abbreviated as PGe—Th) which is the objective product.

Figure 1:
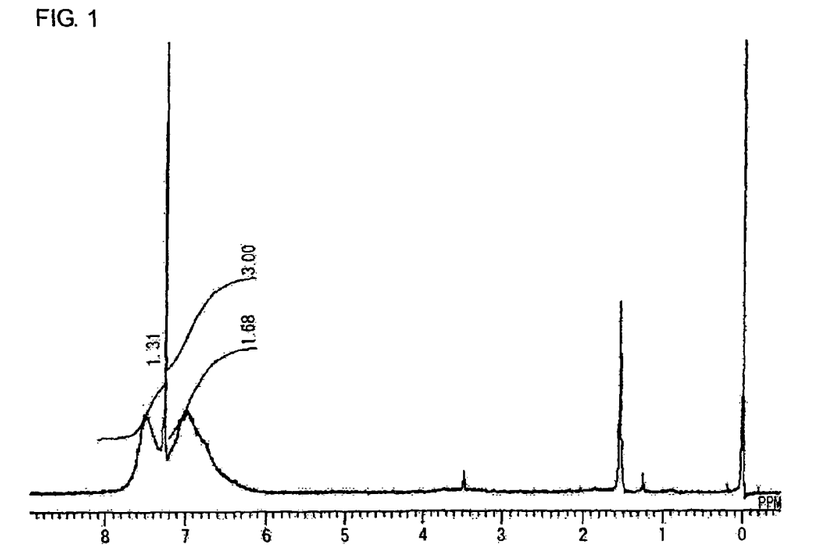
FIG. 1 is a graph showing $^1$H NMR spectrum of a polygermane compound obtained in Example 1.

The measuring result of $^1$H NMR spectrum of the obtained PGe—Th is shown in FIG. 1. The weight average molecular weight Mw and the degree of distribution: Mw (weight average molecular weight)/Mn (number average molecular weight) thereof which were measured by GPC in terms of polystyrene, were respectively 800 and 1.14.

Example 2

Synthesis of 5-methylthiophene-2-yl Group-Substituted Polygermane Compound

By the same operation as in Example 1, except that 2-bromothiophene was changed to 5.0 g (28 mmol) of 2-bromo-5-methylthiophene [manufactured by Tokyo Chemical Industry Co., Ltd.], 1.3 g of a 5-methylthiophene-2-yl group-substituted polygermane compound (hereinafter, abbreviated as PGe—ThM) was obtained.

Figure 2:
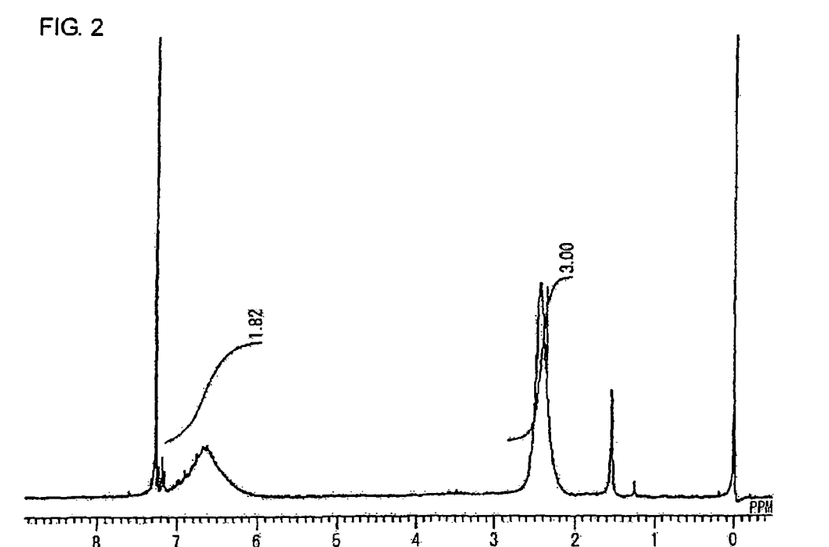
FIG. 2 is a graph showing $^1$H NMR spectrum of a polygermane compound obtained in Example 2.

The measuring result of $^1$H NMR spectrum of the obtained PGe—ThM is shown in FIG. 2. The weight average molecular weight Mw and the degree of distribution: Mw (weight average molecular weight)/Mn (number average molecular weight) thereof which were measured by GPC in terms of polystyrene, were respectively 900 and 1.18.

Example 3

Synthesis of p-thioanisyl Group-Substituted Polygermane Compound

By the same operation as in Example 1, except that 2-bromothiophene was changed to 5.7 g (28 mmol) of 4-bromothioanisole [manufactured by Tokyo Chemical Industry Co., Ltd.], 3.3 g of a p-thioanisyl group-substituted polygermane compound (hereinafter, abbreviated as PGe—Ta) was obtained.

Figure 3:
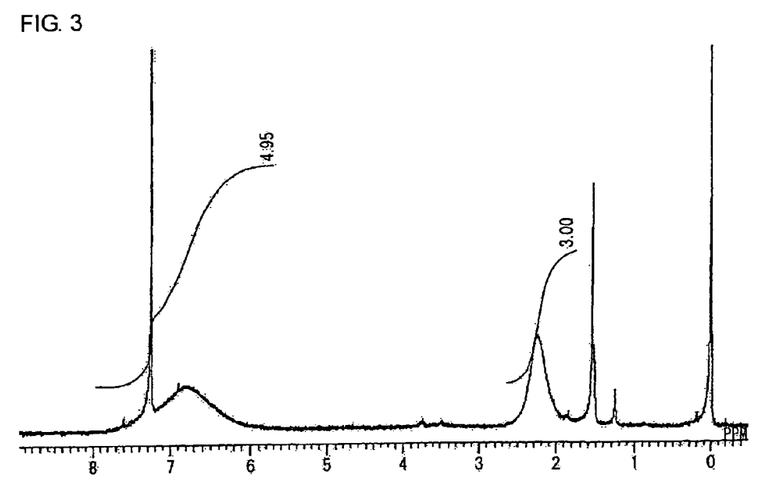
FIG. 3 is a graph showing $^1$H NMR spectrum of a polygermane compound obtained in Example 3.

The measuring result of $^1$H NMR spectrum of the obtained PGe—Ta is shown in FIG. 3. The weight average molecular weight Mw and the degree of distribution: Mw (weight average molecular weight)/Mn (number average molecular weight) thereof which were measured by GPC in terms of polystyrene, were respectively 1,300 and 1.21.

Comparative Example 1

Synthesis of Phenyl Group-Substituted Polygermane Compound

By the same operation as in Example 1, except that 2-bromothiophene was changed to 6.0 g (28 mmol) of bromobenzene [manufactured by Tokyo Chemical Industry Co., Ltd.], 1.2 g of a phenyl group-substituted polygermane compound (hereinafter, abbreviated as PGe—Ph) was obtained.

Figure 4:
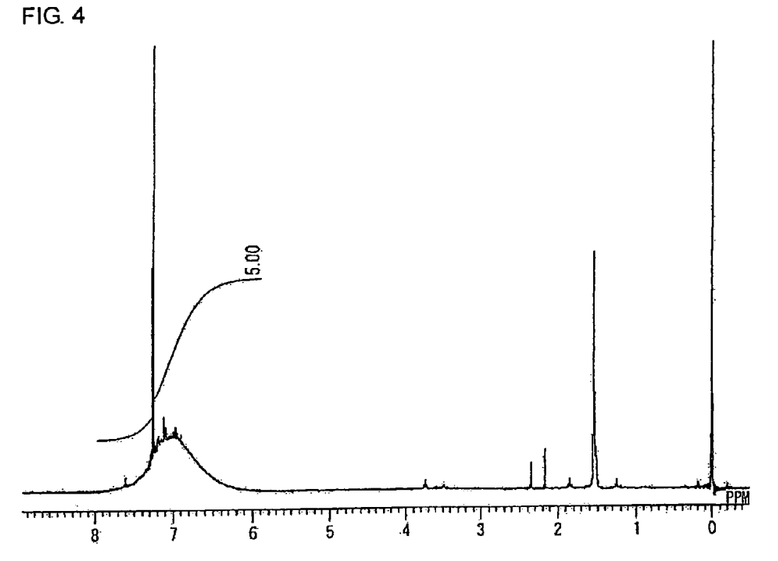
FIG. 4 is a graph showing $^1$H NMR spectrum of a polygermane compound obtained in Comparative Example 1.

The measuring result of $^1$H NMR spectrum of the obtained PGe—Ph is shown in FIG. 4. The weight average molecular weight Mw and the degree of distribution: Mw (weight average molecular weight)/Mn (number average molecular weight) thereof which were measured by GPC in terms of polystyrene, were respectively 900 and 1.13.

Example 4

Heat Resistance Test of Polygermane Compound

Each of the polygermane compounds synthesized in Examples 1 to 3 and Comparative Example 1 was dissolved in toluene to prepare a varnish having a polygermane compound concentration of 3% by mass. The varnish was applied to a glass substrate by a spin coating method (at 1,500 rpm, for 30 seconds). The coating film was prebaked on a hot plate of 80° C. for 10 minutes to remove the solvent in the thin film to obtain each thin film.

Each thin film was heated on a hot plate of 200° C. and the refractive index of each thin film at a wavelength of 633 nm before heating, after heating for 1 minute, and after heating for 5 minutes was measured by an ellipsometer.

The film thickness before heating and the rate of change in the refractive index by heating of each thin film are shown in Table 1. The rate of change in the refractive index was calculated according to the following equation:

Rate of change in refractive index=((refractive index before heating−refractive index after heating for 5 minutes)/refractive index before heating)×100

TABLE 1

| Polygermane compound | Film thickness before heating [nm] | Refractive index | | | Rate of change [%] |
|---|---|---|---|---|---|
| | | Without heating | After heating for 1 minute | After heating for 5 minutes | |
| Example 1 | 68 | 1.82 | 1.82 | 1.81 | 0.44 |
| Example 2 | 74 | 1.76 | 1.76 | 1.75 | 0.45 |
| Example 3 | 80 | 1.81 | 1.80 | 1.78 | 1.72 |
| Comparative Example 1 | 74 | 1.78 | 1.75 | 1.73 | 2.64 |

From the result in Table 1, the rate of change in the refractive index of the thin film containing each of the polygermane compounds of Examples 1 to 3 between before and after heating was smaller than the rate of change in the refractive index of the thin film containing the polygermane compound of Comparative Example 1 between before and after heating, so that the superiority of the present invention was confirmed.

Example 5

Preparation of Polygermane Compound-Containing Acrylic Resin Film 0.15 g of each of the polygermane compounds synthesized in Examples 1 and 2 and Comparative Example 1 was mixed with 0.35 g of tricyclodecane dimethanol diacrylate [trade name: A-DCP; manufactured by Shin-nakamura Chemical Co., Ltd.] which is a polymerizable acrylate compound and 2 mL of toluene. Toluene in the obtained mixed solution was distilled off by an evaporator and thereto, 0.007 g of a peroxide-based thermo-radical polymerization initiator (trade name: Kayaester O-50E; manufactured by Kayaku Akzo Corporation) was added, followed by stirring the resultant mixture to prepare a resin composition (polygermane compound: A-DCP=30:70 (mass ratio)) of the polygermane compound and A-DCP.

The prepared resin composition was dropped onto the center of a slide glass and the slide glass was covered with another slide glass. The slide glasses were heated on a hot plate of 120° C. for 10 minutes to thermo-cure (thermally polymerize) the resin composition. The slide glasses were cooled down to room temperature (about 25° C.) and the upper slide glass was removed to prepare a polygermane compound-containing acrylic resin film (thermo-cured film) on the slide glass.

On the other hand, a resin composition containing no polygermane compound in which 0.50 g of A-DCP and 0.010 g of Kayaester O-50E were mixed was prepared and by the same operation as described above, an acrylic resin film (thermo-cured film) containing no polygermane compound was prepared.

Each thermo-cured film was heated on a hot plate of 200° C. and the refractive index of each thin film at a wavelength of 633 nm before and after heating for 5 minutes was measured by a prism coupler.

The film thickness before heating and the rate of change in the refractive index by heating of each thermo-cured film are shown in Table 2. The rate of change in the refractive index was calculated by the same calculation as in Example 4.

TABLE 2

| Polygermane compound | Film thickness before heating [μm] | Refractive index | | Rate of change [%] |
|---|---|---|---|---|
| | | Without heating | After heating for 5 minutes | |
| Example 1 | 6.1 | 1.58 | 1.57 | 0.63 |
| Example 2 | 6.0 | 1.58 | 1.57 | 0.70 |
| Comparative Example 1 | 4.5 | 1.59 | 1.57 | 1.13 |
| None | | 1.52 | 1.52 | 0.00 |

From the result in Table 2, the rate of change in the refractive index of the acrylic resin film (thermo-cured film) containing each of the polygermane compounds of Example 1 and Example 2 between before and after heating was smaller than the rate of change in the refractive index of the acrylic resin film (thermo-cured film) containing the polygermane compound of Comparative Example 1 between before and after heating, so that the superiority of the present invention was confirmed. In addition, it was confirmed that, by containing the polygermane compounds of Examples 1 and 2, the refractive index of the acrylic resin film could be enhanced.

INDUSTRIAL APPLICABILITY

The thin film and the cured resin containing the polygermane compound of the present invention have characteristics such as a high refractive index, thermal stability, and high transparency, so that they can be utilized as an optical material for a microlens and a core material for a light waveguide.

The following listing of claims will replace all prior versions, and listings, of claims in the application:

The invention claimed is:

1. A polygermane compound comprising a sulfur atom-containing organic group as a group bonded to a germanium atom, wherein the sulfur atom-containing organic group is a group of Formula [1]:

-L-Z  [1]

where L is a single bond, a $C_{1-6}$ alkylene group, or a $C_{4-20}$ arylene group optionally substituted with a $C_{1-6}$ alkyl group; and Z is a $C_{1-20}$ sulfide group, a $C_{1-14}$ cyclic sulfide group optionally substituted with a $C_{1-6}$ alkyl group, a $C_{2-20}$ alkyl group containing a sulfide bond, or a $C_{5-20}$ aralkyl group containing a sulfide bond, with a proviso that when L is a single bond, Z is not a $C_{1-20}$ sulfide group.

2. The polygermane compound according to claim 1, wherein Z is a $C_{1-20}$ sulfide group.

3. The polygermane compound according to claim 1, wherein Z is a $C_{1-4}$ 5-membered ring cyclic sulfide group optionally substituted with a $C_{1-6}$ alkyl group.

4. The polygermane compound according to claim 1, wherein L is a thienylene group optionally substituted with a $C_{1-6}$ alkyl group.

5. A polygermane compound comprising:

a sulfur atom-containing organic group of Formula [1] as a group bonded to a germanium atom, the polygermane compound being obtained by reacting an alkali metal or an alkaline earth metal with a germanium tetrahalide and by further reacting the resultant product with a sulfur atom-containing halide of Formula [2]:

-L-Z [1]

X-L-Z [2]

where L is a single bond, a $C_{1-6}$ alkylene group, or a $C_{4-20}$ arylene group optionally substituted with a $C_{1-6}$ alkyl group; Z is a $C_{1-20}$ sulfide group, a $C_{1-14}$ cyclic sulfide group optionally substituted with a $C_{1-6}$ alkyl group, a $C_{2-20}$ alkyl group containing a sulfide bond, or a $C_{5-20}$ aralkyl group containing a sulfide bond; and X is a halogen atom, with a proviso that when L is a single bond, Z is not a $C_{1-20}$ sulfide group.

6. The polygermane compound according to claim 5, wherein Z is a $C_{1-20}$ sulfide group.

7. The polygermane compound according to claim 6, wherein Z is a $C_{1-4}$ 5-membered ring cyclic sulfide group optionally substituted with a $C_{1-6}$ alkyl group.

8. The polygermane compound according to claim 5, wherein L is a thienylene group optionally substituted with a $C_{1-6}$ alkyl group.

9. A varnish comprising the polygermane compound as claimed in claim 1.

10. A thin film composed of the polygermane compound as claimed in any claim 1.

11. A resin composition comprising:
the polygermane compound as claimed in claim 1; and
a thermoplastic resin and/or a curable resin.

12. A resin molded article produced from the resin composition as claimed in claim 11.

* * * * *